United States Patent
Wald

(10) Patent No.: US 9,439,894 B2
(45) Date of Patent: Sep. 13, 2016

(54) MYELOID DIFFERENTIATION INDUCING AGENTS

(71) Applicant: Case Western Reserve University, Cleveland, OH (US)

(72) Inventor: David Wald, University Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/029,066

(22) Filed: Sep. 17, 2013

(65) Prior Publication Data

US 2014/0018383 A1 Jan. 16, 2014

Related U.S. Application Data

(63) Continuation-in-part of application No. 12/664,469, filed as application No. PCT/US2008/006700 on Jun. 12, 2008, now Pat. No. 8,815,827.

(60) Provisional application No. 60/943,415, filed on Jun. 12, 2007.

(51) Int. Cl.
| | |
|---|---|
| *A61K 31/553* | (2006.01) |
| *A61K 31/00* | (2006.01) |
| *A61K 31/439* | (2006.01) |
| *A61K 45/06* | (2006.01) |
| *C07D 491/18* | (2006.01) |
| *A61K 31/55* | (2006.01) |

(52) U.S. Cl.
CPC ............ *A61K 31/439* (2013.01); *A61K 31/55* (2013.01); *A61K 45/06* (2013.01); *C07D 491/18* (2013.01)

(58) Field of Classification Search
CPC ...................................................... A61K 31/55
USPC ........................................ 514/211.04, 211.11
See application file for complete search history.

(56) References Cited

PUBLICATIONS

Liu et al., "Antitumor effect of securinine (SEC) and its resistance to toxicity of cyclophosphamide (CTX)", Zhongguo Yaolixue Tongbao, vol. 13, No. 6, pp. 529-532 (1997).*
Gupte, Amol, et al., 6-Benzylthioinosine analogues: Promising anti-toxoplasmic agents as inhibitors of the mammalian nucleoside transporter ENT1 (es).
Honma, Yoshia, "Adenine Analogs as Potential Differentiation Therapy Agents for acute Myeloid Leukemia", Drug Development Research 59:14-22 (2003).
Montgomery, John A., "A Comparative Study of the Anticancer Activity of Some S-Substituted Derivatives of 6-Mercapto-purine and their Ribonucleosides", Journal of Medicinal and Pharmaceutical Chemistry, vol. 3, No. 2 (1961.

* cited by examiner

*Primary Examiner* — Kevin E Weddington
(74) *Attorney, Agent, or Firm* — Tarolli, Sundheim, Covell & Tummino LLP

(57) ABSTRACT

Myeloid differentiating agents can be used in the treatment of myeloid proliferative disorders.

4 Claims, 13 Drawing Sheets

ATRA
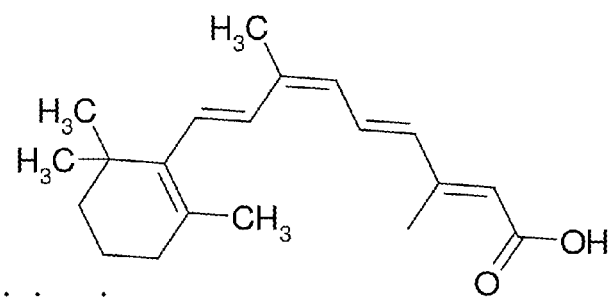
6-benzylthioinosine
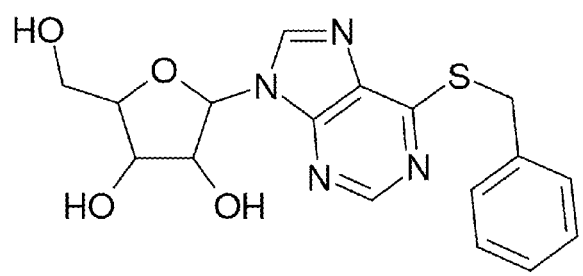
Triciribine
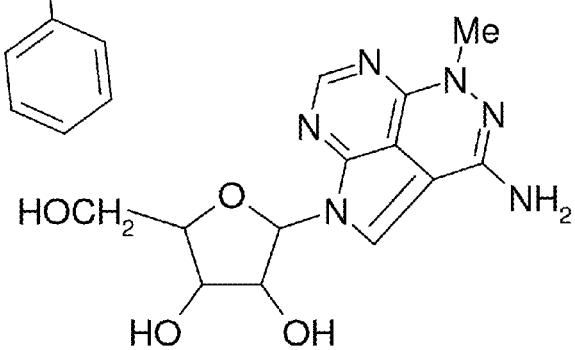
Securinine
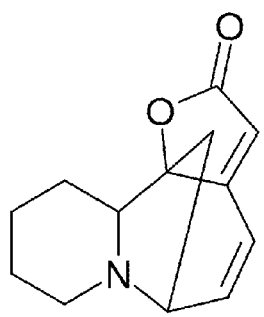
4-methyl[1]benzofuro 3,2-g]quinolin-2-ol
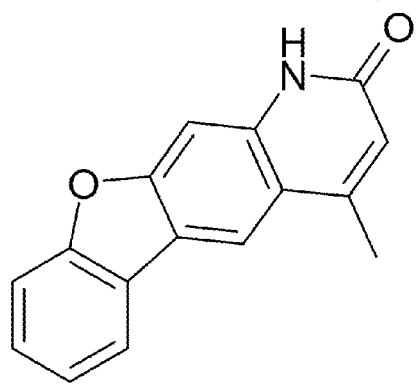
Fig. 1

A.
Patient 1 AML-M4      Patient 2 CML (Gleevec resistant)
Vehicle      6BT           Vehicle      6BT
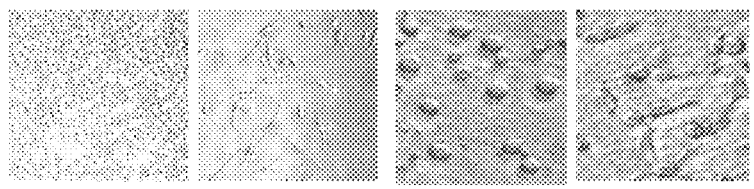
B.                    % NBT reduction
|  | Patient 1 (day7) | Patient 2 (day4) | Pateint 3 (day4) | Patient 4 |
|---|---|---|---|---|
| Vehicle | 6% | 16% | 4% | |
| 6BT | 33% | 57% | 8% | |
| Securinine | 89% | dead | 48% | |
Figs. 7A-B
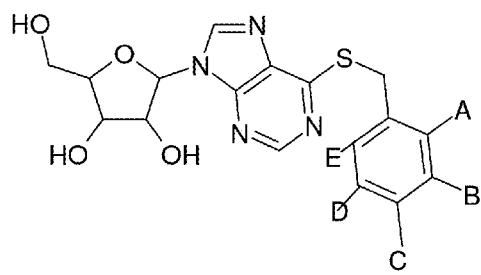
ANALOGUE NUMBER
| Substitutent site | | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| | A | CH3 | F | Cl | | | | | | | | | Cl | | CH3 | | | Cl | | | |
| | B | | | | CH3 | CF3 | NO2 | | | | | | | Cl | | | | | | | F |
| | C | | | | | | | CH3 | OCF3 | Br | OCH3 | tertButyl | | Cl | CH3 | COOCH3 | Cl | Cl | NO2 | CN | |
| | D | | | | | | | | | | | | | | | | | | | | |
| | E | | | | | | | | | | | | F | | CH3 | | | | | | |
Fig. 8

Figs. 9A-D

Moderate activity (Differentiation 90% at 25μM)
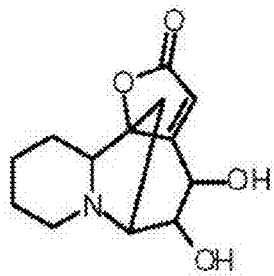
Equivalent activity to parent compound (Differentiation >90% at 15μM)
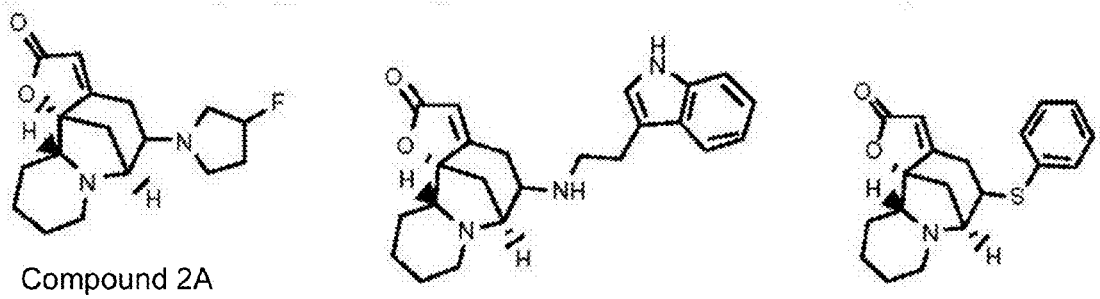
Compound 2A
Superior Activity (Differentiation >90% at 2.5μM)
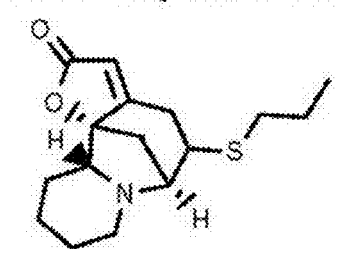
Compound 2B
Fig. 16

MYELOID DIFFERENTIATION INDUCING AGENTS

RELATED APPLICATION

This application is a Continuation-in-Part of U.S. patent application Ser. No. 12/664,469, filed Jun. 25, 2010, which is a National Phase Filing of PCT/US2008/066700, filed Jun. 12, 2008, which claims priority from U.S. Provisional Application No. 60/943,415, filed Jun. 12, 2007, the subject matter of which are incorporated herein by reference in their entirety.

TECHNICAL FIELD

The present invention relates to compounds or therapeutic agents that can be used to promote differentiation of immature myeloid cells, and more particularly to compositions and therapeutics used to treat myeloproliferative disorders and as a myeloablative therapy.

BACKGROUND

Acute Myeloid Leukemia (AML) is one of the most common forms of leukemia in adults and despite advances in treatment the 5 year survival is still less than 50% in adults and significantly lower in the elderly. In fact, the median survival in patients over the age of 56 is less than one year and only 20% of these patients survive two years. Though the prognosis for younger patients is significantly better, disease-free survival at 6 years following complete remission is still only 40% in children and young adults. There is an enormous unmet need for novel therapeutics to improve the morbidity and mortality of these patients. This unmet need is particularly high in the elderly who often cannot tolerate traditional chemotherapy due to toxicities. Though there have been a number of clinical trials, there has been little improvement in overall survival in this age group over the last 30 years.

Acute myeloid leukemia is a broad range of disorders that are all characterized by leukemic cells that have a differentiation arrest. AML can be classified morphologically according to the French-American-British criteria by the degree of differentiation as well as extent of cell maturation as M0-M7. Treatment for all subtypes of AML is very similar, except for acute promyelocytic leukemia (APL, M3 subtype). Traditional therapy involves combination systemic chemotherapy. Several different approaches are utilized; however, they usually involve an induction therapy with cytarabine and a second chemotherapeutic such as daunorubicin or idarubicin and consolidation therapy with either a bone marrow transplant or additional chemotherapy. Besides significant side effects from the traditional chemotherapeutics, the efficacy of these agents in treating AML is poor.

To date the only exception to the poor treatment options for AML is the remarkable success of all-trans-retinoic acid ATRA for one relatively uncommon subtype (5-10% of AML), acute promyelocytic leukemia (APL). Utilizing a combination of ATRA and chemotherapy, the long term survival and presumed cure of 75-85% of patients is possible. ATRA illustrates the great promise for new agents with greater efficacy and less toxicity. In fact, elderly patients with APL who cannot tolerate traditional chemotherapy can achieve complete remission with therapies that utilize ATRA.

ATRA's success stems from the fact that AML is a clonal disease characterized by the arrest of differentiation of immature myeloid cells. ATRA overcomes this block in differentiation by forcing leukemic cells to terminally differentiate so that they are no longer capable of dividing. ATRA is successful in APL due to its ability to reverse the dominant negative effects of the PML-RAR fusion protein created by a chromosomal translocation, classically t(15;17) (q22;q21). This fusion protein interacts with the retinoid x receptor (RXR), nuclear corepressors and histone deacetylase (HDAC) resulting in repression of transcription that leads to the block in differentiation. At pharmacologic doses, ATRA is able to overcome the repression of transcription and differentiation results. Unfortunately, APL is a rare subtype of AML and ATRA has not been found to be clinically useful for other subtypes.

Though many compounds have been shown to have some differentiation-inducing effects in vitro, their clinical utility has been limited by either suboptimal differentiation-inducing capacity and/or toxicity. For example, Vitamin D3 induces potent differentiation, however, it also causes severe hypercalcemia at the required dose. Treatments that promote the differentiation of immature myeloid cells hold considerable promise in improving the long term survival of AML patients while avoiding some of the toxicities of traditional chemotherapy. Treatment of leukemia could be revolutionized by novel compounds due to their potential to cure leukemia and provide elderly patients with alternative non-toxic regimens.

SUMMARY

Embodiments described herein relate to compounds or therapeutic agents that can be used as myeloid differentiation inducing agents as well as to the use of such compounds or agents to treat myeloid proliferative disorders (e.g., acute myeloid leukemia). The myeloid differentiation agents can include securinine or securinine analogues that when administered to immature myeloid cells of a subject can promote differentiation of the immature myeloid cells to more mature cells that do not readily proliferate. Agents in accordance with the invention have a high-potency and low toxicity in mammalian subjects and can be used in the treatment of myeloid disorders, such as myeloproliferative disorders, acute myeloid leukemia and auto immune disease, to induce and/or promote differentiation of the myeloid cells. The agents can also be used as a myeloablative agent in conjunction with bone marrow transplantation and stem cell therapies.

In some embodiments, the securinine or securinine analogue can include the general formula:

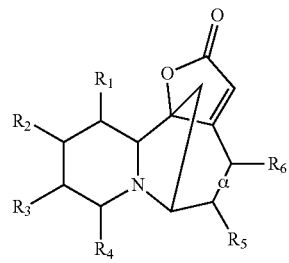

wherein α is a single or double bond;

$R_1$, $R_2$, $R_3$, $R_4$, $R_5$, and $R_6$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof;

wherein adjacent R groups (e.g., $R_1$ and $R_2$, or $R_3$ and $R_4$, or $R_5$ and $R_6$) may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

The myeloid differentiating agents can be used alone or in combination with other differentiating agents or other antiproliferative agents or chemotherapeutic agents to treat myeloid proliferative disorders, such as leukemia. The myeloid differentiation agents can also be administered to a subject in conjunction with myeloablative therapy, for example, prior to the subject receiving bone marrow transplantation or stem cell therapy.

The myeloid differentiating agents can also be provided in a pharmaceutical composition either alone or with one or more agents.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 1 illustrates differentiation-inducing compounds that exhibit structures, which are unrelated to ATRA.

FIGS. 7(A-B) illustrate 6BT and securinine have potent differentiation and cell death effects on primary leukemic samples. Primary patient leukemic samples were stained with CD34+ and sorted by flow cytometry. Leukemic cells were treated with the indicated compounds (6BT 10 mM Securinine 15 mM) for up to 7 days. A. Representative pictures showing morphological differentiation of primary patient samples B. 6BT and Securinine treated primary leukemic cells show either differentiation by NBT reduction or cell death.

FIG. 8 illustrate the benzyl ring is important in 6BT's differentiation-inducing activity. The specific substitutents of the 20 analogues tested are illustrated.

FIG. 16 illustrates securinine analogues that were synthesized and their relative activities as measured by NBT reduction assay in HL-60 cells.

DETAILED DESCRIPTION

Figure 2:
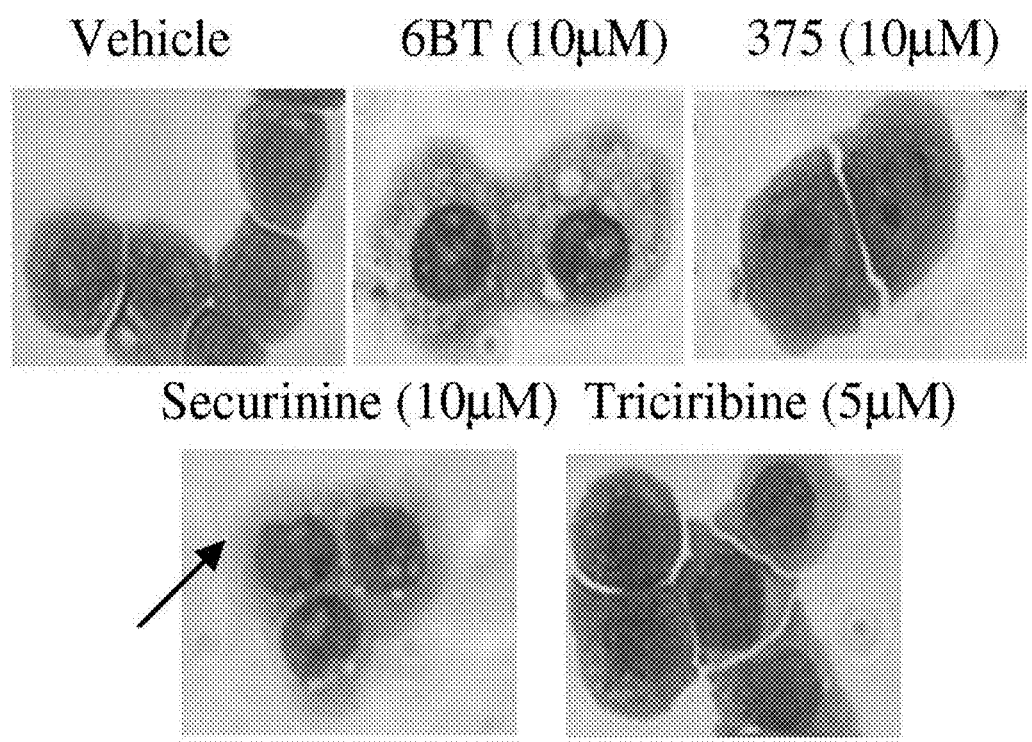
FIG. 2 illustrates images showing compounds described herein induce morpohologic changes consistent with monocytic differentiation. HL-60 cells were treated with the indicated compounds for 4 days. Cytospin preparations were prepared and the cells were stained with Wright-Giemsa stain. Note arrow points to indented nucleus characteristic of monocytes.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p1-92, Elesevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)($O^-$)$_2$), phosphinato (—P(O)($O^-$)), phospho (—PO$_2$), and phosphino (—PH$_2$); and the hydrocarbyl moieties C$_1$-C$_{24}$ alkyl, C$_2$-C$_{24}$ alkenyl, C$_2$-C$_{24}$ alkynyl, C$_5$-C$_{20}$ aryl, C$_6$-C$_{24}$ alkaryl, and C$_6$-C$_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compounds or therapeutic agents that can be used to induce differentiation of immature myeloid cells as well as to methods and assays of identifying therapeutic agents or compounds capable of inducing differentiation of immature myeloid cells. Agents in accordance with the invention have a high-potency and low toxicity in mammalian subjects and can be used in the treatment of myeloid disorders, such as myeloproliferative disorders, acute myeloid leukemia and auto immune disease, to induce and/or promote differentiation of the myeloid cells. The agents can also be used as a myeloablative agent in conjunction with bone marrow transplantation and stem cell therapies.

The agents in accordance with the present invention can be used alone or in combination with other differentiation inducing agents, anti-proliferative agents, and/or chemotherapeutic agents for the treatment of proliferative and/or other neoplastic disorders.

In an aspect of the present invention, the agents can be identified using a novel high-troughput screen that is biased to identify agents that have both a high potency and low toxicity. The screen measures the differentiation of HL-60 leukemic cells using a quantitative nitroblue tetrazolium (NBT) reduction assay. Screening HL-60 cells, human promyelocytic cells, is advantageous as they have been used extensively as a cell line to study myeloid differentiation. Though promyelocytic cells, HL-60 cells are actually derived from a patient with acute myeloblastic leukemia with maturation, FAB-M2. This cell line has been shown to be an excellent model to study myeloid differentiation as it undergoes terminal differentiation to either granulocytic or monocytic pathways with numerous known compounds. The differentiated cells demonstrate all of the expected functional properties such as chemotaxis, bacterial killing, ingestion, and respiratory burst activity.

Nitroblue Tetrazolium (NBT) reduction has been widely demonstrated to provide a very accurate correlation to the extent of myeloid differentiation to both granulocytic and monocytic pathways. This technique has also been widely exploited in HL-60 cells to analyze myelomonocytic differentiation. In fact, it has been routinely demonstrated for over 20 years that the NBT test provides an extremely close correlation with the morphology of the differentiated cells.

The NBT screen works due to changes in the oxidoreductases during differentiation that lead to increases in rates of NBT reduction. NBT is reduced due to the production of superoxide that is catalyzed by an NADPH oxidase. This enzyme is inactive in resting cells, therefore, it is necessary to treat the cells with PMA to generate an oxidative burst. NBT is reduced by superoxide from a soluble yellow compound to isoluble blue formazan granules whose formation can be monitored spectrophotometrically at 560 nm as the unreduced dye has minimal absorbance at this wavelength. A quantitative NBT reduction assay is ideal for this type of screen as it is simple, sensitive, quantitative, requires minimal cells, has been proven to have low well to well variability, and the amount of reduced NBT is proportional to the number of cells reducing the dye as well as the amount reduced by each cell.

By way of example, duplicate plates of HL-60 cells can be cultured at a density of 5×10$^4$ cells/ml with 10 μM of each compound in 96 well plates for 5 days. To determine the relative capability for a compound to induce differentiation compared to known potent inducers, each plate destined for the NBT reduction assay can include wells with 0.1% DMSO (vehicle control) and 1 μM ATRA. This approach eliminates any slight day to day variation in NBT reduction values and allows the discovery of compounds with similar or greater efficacy to ATRA. Differentiation is determined in the 96 well plates by incubating the cells with 1 mg/ml of NBT and 200 ng/ml of PMA as the stimulant for the respiratory burst for 35 minutes at 37° C. The reaction can then be stopped with HCL and the formazan will be solubilized with DMSO. Finally, the reaction mixture will be read spectrophotometricaly at 560 nm in a plate reader.

In some embodiments, the myeloid differentiation agents can include securinine or securinine analogues that when administered to immature myeloid cells of a subject can promote differentiation of the immature myeloid cells to more mature cells that do not readily proliferate. The securinine or securinine analogues can be identified using the NBT reduction assay described herein.

In other embodiments, the securinine or securinine analogue can include a compound having the following general formula:

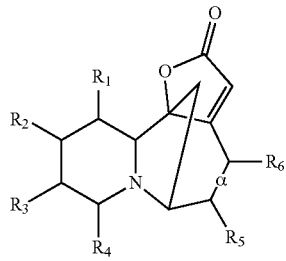

wherein α is a single or double bond;

$R_1$, $R_2$, $R_3$, $R_4$, $R_5$, and $R_6$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof;

wherein adjacent R groups (e.g., $R_1$ and $R_2$, or $R_3$ and $R_4$, or $R_5$ and $R_6$) may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

In other embodiments, the securinine or securinine analogue can include a compound having the following general formula:

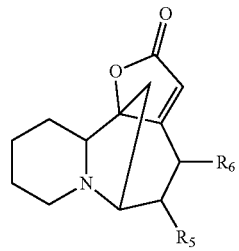

where $R_5$ and $R_6$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), combinations thereof; and pharmaceutically acceptable salts thereof.

Examples of securinine or securinine analogues that when administered to immature myeloid cells of a subject can promote differentiation of the immature myeloid cells to more mature cells that do not readily proliferate include the following compounds:

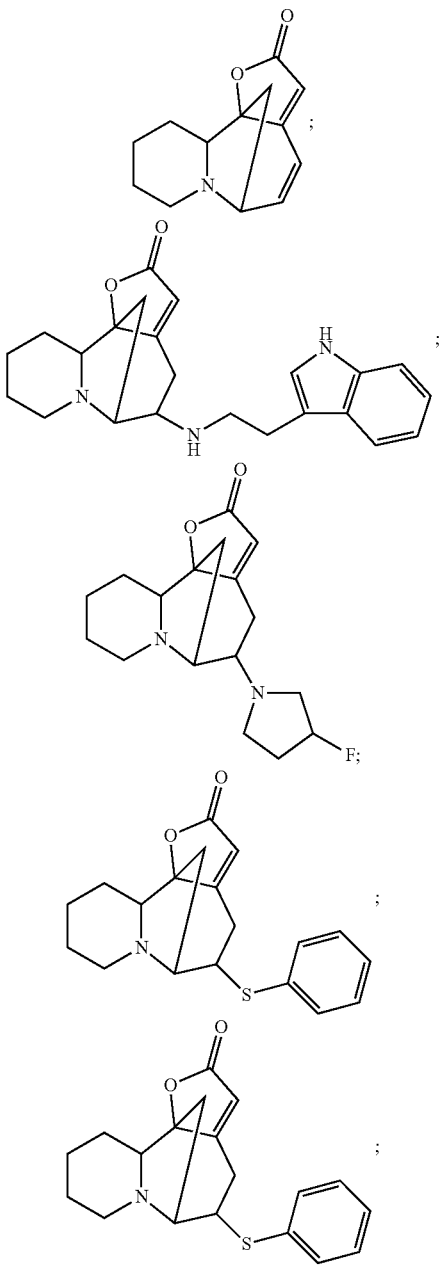

and pharmaceutically acceptable salts thereof.

The myeloid differentiation agents described herein can be administered in a therapeutically effective amount to a patient or subject with a disorder characterized by arrest of differentiation of immature myeloid cells. These disorders can include, for example, myeloproliferative disorders, such as leukemia, and immunity related diseases.

Treatment of a patient by administration of myeloid differentiation agent of the present invention encompasses chemoprevention in a patient susceptible to developing myeloid leukemia (e.g., at a higher risk, as a result of genetic predisposition, environmental factors, or the like) and/or in cancer survivors at risk of cancer recurrence, as well as treatment of a myeloid leukemia patient by inhibiting or causing regression of a disorder or disease.

In some embodiments, effective amounts are amounts of the myeloid differentiation agent effective to induce or promote differentiation of the immature myeloid cells in the subject being treated without being cytotoxic to the subject.

The immature myeloid differentiation inducing agents can be provided in the form of pharmaceutical compositions. The pharmaceutical compositions can be administered to any mammal that can experience the beneficial effects of the myeloid differentiation inducing agents of the present invention. Foremost among such animals are humans, although the present invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively or concurrently, administration can be by the oral route. Particularly preferred is oral administration. The dosage administered will be dependent upon the age, health, and weight of the patient, kind of concurrent treatment, if any, frequency of treatment, and the nature of the effect desired.

In addition to the pharmacologically active compounds, the pharmaceutical preparations of the myeloid differentiation inducing agents can contain suitable pharmaceutically acceptable carriers comprising excipients and auxiliaries that facilitate processing of the active agents into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active agents with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Formulations for parenteral administration include aqueous solutions of the active compounds in water-soluble form, for example, water-soluble salts and alkaline solutions. Especially preferred salts are maleate, fumarate, succinate, S,S tartrate, or R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

In a further aspect of the invention, the myeloid differentiation inducing agents can be used in combination and adjunctive therapies for treating proliferative disorders.

The phrase "combination therapy" embraces the administration of the myeloid differentiation inducing agents and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" encompasses treatment of a subject with agents that reduce or avoid side effects associated with the combination therapy of the present invention, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

The mammalian disease treated by the combination therapy can include proliferative diseases, such as neoplastic disorders (e.g., leukemia) and autoimmune dysfunctions as well as viral and microbial infections. Besides being useful for human treatment, the combination therapy is also useful for veterinary treatment of companion animals, exotic and farm animals, including rodents, horses, dogs, and cats.

In another aspect of the invention, the therapeutic agents administered in combination therapy with the myeloid differentiation inducing agents can comprise at least one anti-proliferative agent selected from the group consisting of a chemotherapeutic agent, an antimetabolite, an antitumorgenic agent, an antimitotic agent, an antiviral agent, an antineoplastic agent, an immunotherapeutic agent, and a radiotherapeutic agent.

The phrase "anti-proliferative agent" can include agents that exert antineoplastic, chmotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development, which could be included in the present invention by combination drug chemotherapy. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endotheliai cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

A first family of anti-proliferative agents, which may be used in combination therapy with the myeloid differentiation inducing agents consists of antimetabolite-type anti-proliferative agents. Antimetabolites are typically reversible or irreversible enzyme inhibitors, or compounds that otherwise interfere with the replication, translation or transcription of nucleic acids. Examples of antimetabolite antineoplastic agents that may be used in the present invention include, but are not limited to acanthifolic acid, aminothiadiazole, anastrozole, bicalutamide, brequinar sodium, capecitabine, carmofur, Ciba-Geigy CGP-30694, cladribine, cyclopentyl cytosine, cytarabine phosphate stearate, cytarabine conjugates, cytarabine ocfosfate, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, finasteride, floxuridine, fludarabine phosphate, N-(2'-furanidyl)-5-fluorouracil, Daiichi Seiyaku FO-152, fluorouracil (5-FU), 5-FU-fibrinogen, isopropyl pyrrolizine, Lilly LY-188011, Lilly LY-264618, methobenzaprim, methotrexate, Wellcome MZPES, nafarelin, norspermidine, nolvadex, NCI NSC-127716, NCI NSC-264880, NCI NSC-39661, NCI NSC-612567, Warner-Lambert PALA, pentostatin, piritrexim, plicamycin, Asahi Chemical PL-AC, stearate; Takeda TAC-788, thioguanine, tiazofurin, Erbamont TIF, trimetrexate, tyrosine kinase inhibitors, tyrosine protein kinase inhibitors, Taiho UFT, toremifene, and uricytin, all of which are disclosed in U.S. Pat. No. 6,916,800, which is herein incorporated by reference in its entirety.

A second family of anti-proliferative agents, which may be used in combination therapy with the myeloid differentiation inducing agents of the present invention, consists of alkylating-type anti-proliferative agents. The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue. Examples of alkylating-type anti-proliferative agents that may be used in the present invention include, but are not limited to, Shionogi 254-S, aldo-phosphamide analogues, altretamine, anaxirone, Boehringer Mannheim BBR-2207, bestrabucil, budotitane, Wakunaga CA-102, carboplatin, carmustine (BiCNU), Chinoin-139, Chinoin-153, chlorambucil, cisplatin, cyclophosphamide, American Cyanamid CL-286558, Sanofi CY-233, cyplatate, dacarbazine, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, etoposide phosphate, fotemustine, Unimed G-6-M, Chinoin GYKI-17230, hepsul-fam, ifosfamide, iproplatin, lomustine, mafosfamide, mitolactol, mycophenolate, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, thiotepa, Yakult Honsha SN-22, spiromus-tine, Tanabe Seiyaku TA-077, tauromustine, temozolomide, teroxirone, tetraplatin and trimelamol.

A third family of anti-proliferative agents that may be used in combination therapy with the myeloid differentiation inducing agents of the present invention consists of antibiotic-type anti-proliferative agents. Examples of antibiotic-type anti-proliferative agents that may be used in the present invention include, but are not limited to Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of anti-proliferative agents that may be used in combination therapy with the myeloid differentiation inducing agents of the present invention consists of synthetic nucleosides. Several synthetic nucleosides have been identified that exhibit anticancer activity. A well known nucleoside derivative with strong anticancer activity is 5-fluorouracil (5-FU). 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anticancer activity have been described in U.S. Pat. No. 4,336,381, which is herein incorporated by reference in its entirety.

A fifth family of anti-proliferative agents that may be used in combination therapy with the myeloid differentiation inducing agents of the present invention consists of hormonal agents. Examples of hormonal-type anti-proliferative agents that may be used in the present invention include, but are not limited to Abarelix; Abbott A-84861; Abiraterone acetate; Aminoglutethimide; anastrozole; Asta Medica AN-207; Antide; Chugai AG-041R; Avorelin; aseranox; Sensus B2036-PEG; Bicalutamide; buserelin; BTG CB-7598; BTG CB-7630; Casodex; cetrolix; clastroban; clodronate disodium; Cosudex; Rotta Research CR-1505;

cytadren; crinone; deslorelin; droloxifene; dutasteride; Elimina; Laval University EM-800; Laval University EM-652; epitiostanol; epristeride; Mediolanum EP-23904; EntreMed 2-ME; exemestane; fadrozole; finasteride; flutamide; formestane; Pharmacia & Upjohn FCE-24304; ganirelix; goserelin; Shire gonadorelin agonist; Glaxo Wellcome GW-5638; Hoechst Marion Roussel Hoe-766; NCI hCG; idoxifene; isocordoin; Zeneca ICI-182780; Zeneca ICI-118630; Tulane University JO15X; Schering Ag J96; ketanserin; lanreotide; Milkhaus LDI-200; letrozol; leuprolide; leuprorelin; liarozole; lisuride hydrogen maleate; loxiglumide; mepitiostane; Leuprorelin; Ligand Pharmaceuticals LG-1127; LG-1447; LG-2293; LG-2527; LG-2716; Bone Care International LR-103; Lilly LY-326315; Lilly LY-353381-HCl; Lilly LY-326391; Lilly LY-353381; Lilly LY-357489; miproxifene phosphate; Orion Pharma MPV-2213ad; Tulane University MZ-4-71; nafarelin; nilutamide; Snow Brand NKS01; octreotide; Azko Nobel ORG-31710; Azko Nobel ORG-31806; orimeten; orimetene; orimetine; ormeloxifene; osaterone; Smithkline Beecham SKB-105657; Tokyo University OSW-1; Peptech PTL-03001; Pharmacia & Upjohn PNU-156765; quinagolide; ramorelix; Raloxifene; statin; sandostatin LAR; Shionogi S-10364; Novartis SMT-487; somavert; somatostatin; tamoxifen; tamoxifen methiodide; teverelix; toremifene; triptorelin; TT-232; vapreotide; vorozole; Yamanouchi YM-116; Yamanouchi YM-511; Yamanouchi YM-55208; Yamanouchi YM-53789; Schering AG ZK-1911703; Schering AG ZK-230211; and Zeneca ZD-182780.

A sixth family of anti-proliferative agents that may be used in combination therapy with the myeloid differentiation inducing agents of the present invention consists of a miscellaneous family of antineoplastic agents including, but not limited to alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristo-Myers BMY-40481, Vestar boron-10, bromofosfamide, Wellcome BW-502, Wellcome BW-773, calcium carbonate, Calcet, Calci-Chew, Calci-Mix, Roxane calcium carbonate tablets, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Cell Pathways CP-461, Yakult Honsha CPT-11, crisnatol, curaderm, cytochalasin B, cytarabine, cytocytin, Merz D-609, DABIS maleate, dacarbazine, datelliptinium, DFMO, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel, Encore Pharmaceuticals E7869, elliprabin, elliptinium acetate, Tsumura EPMTC, ergotamine, etoposide, etretinate, Eulexin®, Cell Pathways Exisulind® (sulindac sulphone or CP-246), fenretinide, Merck Research Labs Finasteride, Florical, Fujisawa FR-57704, gallium nitrate, gemcitabine, genkwadaphnin, Gerimed, Chugai GLA-43, Glaxo GR-63178, grifolan NMF-5N, hexadecylphosphocholine, Green Cross HO-221, homoharringtonine, hydroxyurea, BTG ICRF-187, ilmofosine, irinotecan, isoglutamine, isotretinoin, Otsuka JI-36, Ramot K-477, ketoconazole, Otsuak K-76COONa, Kureha Chemical K-AM, MECT Corp KI-8110, American Cyanamid L-623, leucovorin, levamisole, leukoregulin, lonidamine, Lundbeck LU-23-112, Lilly LY-186641, Materna, NCI (US) MAP, marycin, Merrel Dow MDL-27048, Medco MEDR-340, megestrol, merbarone, merocyanine derivatives, methylanilinoacridine, Molecular Genetics MGI-136, minactivin, mitonafide, mitoquidone, Monocal, mopidamol, motretinide, Zenyaku Kogyo MST-16, Mylanta, N-(retinoyl)amino acids, Nilandron; Nisshin Flour Milling N-021, N-acylated-dehydroalanines, nafazatrom, Taisho NCU-190, Nephro-Calci tablets, nocodazole derivative, Normosang, NCI NSC-145813, NCI NSC-361456, NCI NSC-604782, NCI NSC-95580, octreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, retinoids, Encore Pharmaceuticals R-flurbiprofen, Sandostatin; Sapporo Breweries RBS, restrictin-P, retelliptine, retinoic acid, Rhone-Poulenc RP-49532, Rhone-Poulenc RP-56976, Scherring-Plough SC-57050, Scherring-Plough SC-57068, seienium(selenite and selenomethionine), SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, Sugen SU-101, Sugen SU-5416, Sugen SU-6668, sulindac, sulindac sulfone; superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, Zileuton, ursodeoxycholic acid, and Zanosar.

The myeloid differentiation inducing agents described herein can allow the combination therapeutic agents and therapies of the present invention to be administered at a low dose, that is, at a dose lower than has been conventionally used in clinical situations.

A benefit of lowering the dose of the combination therapeutic agents and therapies of the present invention administered to a mammal includes a decrease in the incidence of adverse effects associated with higher dosages. For example, by the lowering the dosage of a chemotherapeutic agent such as methotrexate, a reduction in the frequency and the severity of nausea and vomiting will result when compared to that observed at higher dosages. Similar benefits are contemplated for the compounds, compositions, agents and therapies in combination with the inhibitors of the present invention.

By lowering the incidence of adverse effects, an improvement in the quality of life of a patient undergoing treatment for cancer is contemplated. Further benefits of lowering the incidence of adverse effects include an improvement in patient compliance, a reduction in the number of hospitalizations needed for the treatment of adverse effects, and a reduction in the administration of analgesic agents needed to treat pain associated with the adverse effects.

Alternatively, the methods and combination of the present invention can also maximize the therapeutic effect at higher doses.

When administered as a combination, the therapeutic agents can be formulated as separate compositions which are given at the same time or different times, or the therapeutic agents can be given as a single composition.

EXAMPLE 1

Identification of Novel Differentiation-inducing Compounds

To discover novel AML differentiation-inducing compounds a rapid high-throughput screen (HTS) was developed and optimized. The screen was designed to be biased to identify compounds that, unlike the majority of known differentiation-inducing agents, have both high potency and low toxicity. The screen measured the differentiation of HL-60 leukemic cells using a quantitative Nitroblue Tetrazolium (NBT) reduction assay, a test that is used extensively as a measure of functional myelomonocytic differentiation. The basis for the screen is unreduced NBT exists as a yellow soluble dye. Differentiated leukemic cells are capable of producing a respiratory burst that can reduce NBT into a blue insoluble compound that can be measured spectrophotometrically. This forward chemical genetics approach allowed the discovery of novel compounds that can act on targets not previously known to be "drugable." As only live cells can reduce NBT, the screen is biased in identifying relatively nontoxic compounds.

To perform the screen, duplicate plates of HL-60 cells are cultured at a density of $5 \times 10^4$ cells/ml with 10 μM of each compound in 96 well plates for 5 days. To determine the relative capability for a compound to induce differentiation compared to known potent inducers, each plate destined for the NBT reduction assay can include wells with 0.1% DMSO (vehicle control) and 1 μM ATRA. This approach eliminates any slight day to day variation in NBT reduction values and allows the discovery of compounds with similar or greater efficacy to ATRA. Differentiation is determined in the 96 well plates by incubating the cells with 1 mg/ml of NBT and 200 ng/ml of PMA as the stimulant for the respiratory burst for 35 minutes at 37° C. The reaction will then be stopped with HCL and the formazan will be solubilized with DMSO. Finally, the reaction mixture will be read spectrophotometricaly at 560 nm in a plate reader.

From this screen, in addition to several known inducers such as ATRA, 17 novel compounds structurally unrelated to any previously described differentiation-inducers were identified and verified by secondary screening (~18,000 compounds screened in total) (Table 1).

TABLE 1

Partial list of novel differentiation-inducing compounds identified. Note compounds previously known to induce differentiation are in bold. Securinine was identified from two libraries.

| Lopac Library | Prestwick Library | Spectrum Library |
|---|---|---|
| Ciprofibrate | Securinine | Securinine |
| TTNPB | ATRA | Tretinon |
| Retinoic acid | Isoretinoin | Isotretinon |
| 13-cis-retinoic acid | | Acivicin |
| | | Aclacinomycin A1 |

National Cancer Institute Library
Triciribine
6-Benzylthioinosine
4-methyl[1]benzofuro[3,2-g]quinolin-2-ol (375)
A-7, 2M2PM
3-(2,4-dithioxo-1,3-thiazolidin-3-yl)propanoic acid
N-(3-phenyl-2-propenylidene)-9H-fluoren-2-amine
6-((((6-chloro-4H-1,3-benzodioxin-8-yl)methyl)thio)-3 (cyclopropylmethyl)-1,2,3,4-tetrahydro-1,3,5-triazine
3,14,16-trihydroxycard-20(22)-enolid
20-(6-methoxy-2H-1,3-benzoxazin-3(4H)-yl)pregnan-3-ol Compounds were ranked based upon activity level in the NBT assay and four of the top compounds, all of which are structurally unrelated to ATRA, were further analyzed (FIG. 1).

6BT and Securinine Induce Potent Monocytic Differentiation

Figure 3:
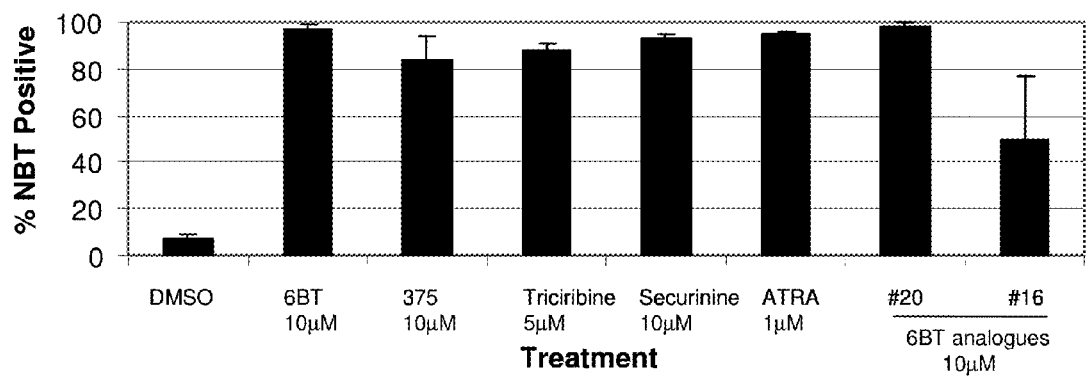
FIG. 3 illustrates a graph showing compounds induce potent NBT reduction activity. HL-60 cells were treated with the indicated compounds for 4 days and the NBT reduction assay was performed. Only the 6BT analogues that showed NBT reduction activity are shown. The percentage of NBT positive cells was calculated by counting at least 200 cells under a light microscope.

Data demonstrating the capability of these compounds to induce differentiation as measured by morphologic changes, up-regulation of the cell surface markers, and NBT reduction can be seen in FIGS. 2 and 3 and Table 2. 6BT and Securinine induce clear morphologic changes suggestive of monocytic differentiation. 6BT leads to a macrophage-like cell in which the cells adhere to the tissue culture plate, the nucleus condenses and loses its prominent nucleoi, and the cytoplasm becomes abundant and vacuolated. Securinine induces monocytic differentiation as evidenced by indented and condensed nuclei that lack prominent nucleoli and more abundant and vacuolated cytoplasm. In contrast, 375 and Triciribine lead to reproducible, but less pronounced changes. 375 induces cells to become greatly enlarged, while Triciribine leads to an increase in cytoplasm and the attachment of some cells to the tissue culture plate. Flow cytometric analysis supports that 6BT and Securinine both lead to monocytic differentiation (Table 2). While the cell surface marker CD11b is induced during both granulocytic and monocytic differentiation, the marker CD14 is specific to monocytic differentiation. 6BT, Securinine, and the known monocytic differentiation-inducing agent Vitamin D3 induce CD 14 and CD 11b, while ATRA, a granulocytic differentiation-inducing agent, primarily induces CD11b. From the NBT reduction assay, 6BT and Securinine have similar activity to ATRA in HL-60 cells as ~95% of cells are differentiated by all three of these compounds (FIG. 3).

TABLE 2

6BT and Securinine induce immunophenotypic changes consistent with monocytic maturation. HL-60 cells were treated with the indicated compounds for 4 days, the cells were stained with CD11b-PE and CD14-FITC, and flow cytometric analysis was performed.

| Treatment | CD11b positive | CD14 positive |
|---|---|---|
| DMSO Control | 10% | 6% |
| ATRA (1 μM) | 77% | 8% |
| Vitamin D (100 nM) | 90% | 65% |
| 6BT (10 μM) | 56% | 64% |
| 375 (10 μM) | 64% | 19% |
| Triciribine (5 μM) | 76% | 10% |
| Securinine (10 μM) | 87% | 86% |

Figure 4:
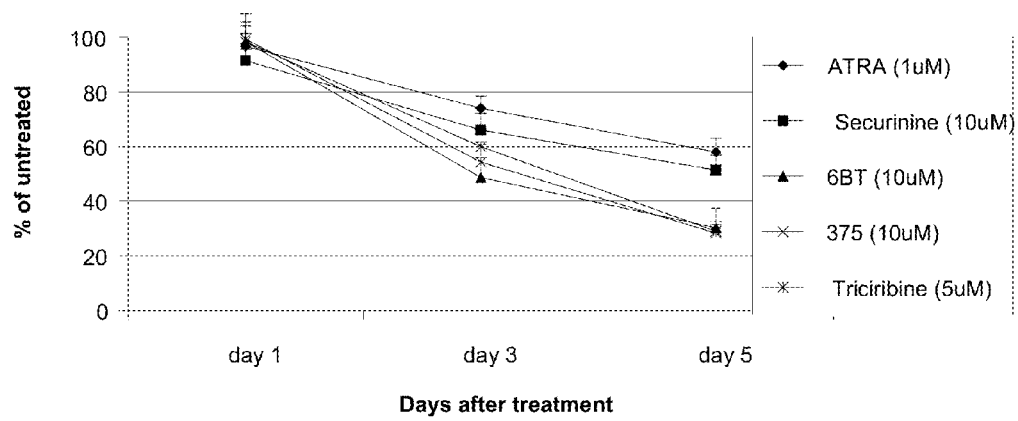
FIG. 4 is illustrates a graph showing compounds inhibit the proliferation of HL-60 cells. Cells were treated with the indicated compounds for up to 5 days and the number of cells present at specific times points was assessed by counting at least 200 cells with a hematocytometer. Experiment results represent the number of cells in the treated well divided by the number of cells in a vehicle treated well at the same time point. Results are an average of three experiments.
Figure 5:
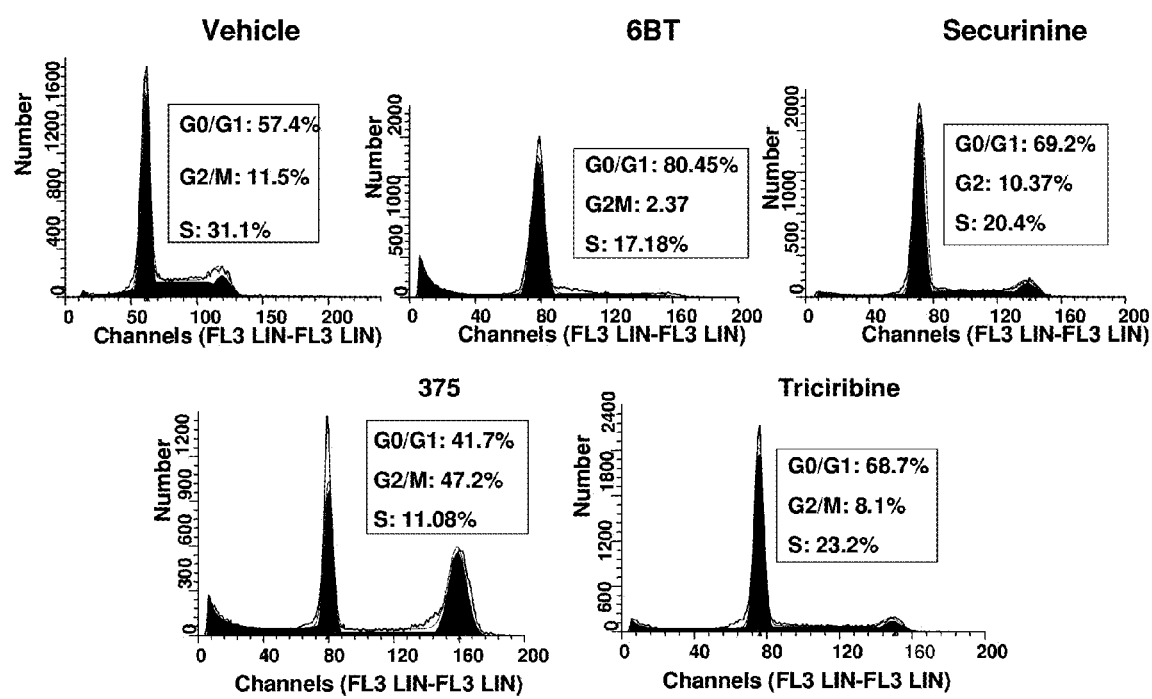
FIG. 5 illustrates histograms showing compounds that induce alterations of the cell cycle. HL-60 cells were treated with the indicated compounds for 4 days and the cells were stained with propidium iodide and analyzed by flow cytometry.

Novel Differentiation-inducing Agents Inhibit Proliferation and Induce Terminal Differentiation As clinically useful agents should lead to terminal differentiation in which the malignant cells lose their ability to proliferate after a limited number of cell divisions, we investigated the effects of the compounds on the inhibition of proliferation of leukemic cells. The proliferation of HL-60 cells was potently inhibited by all four novel compounds (FIG. 4).

Figure 6:
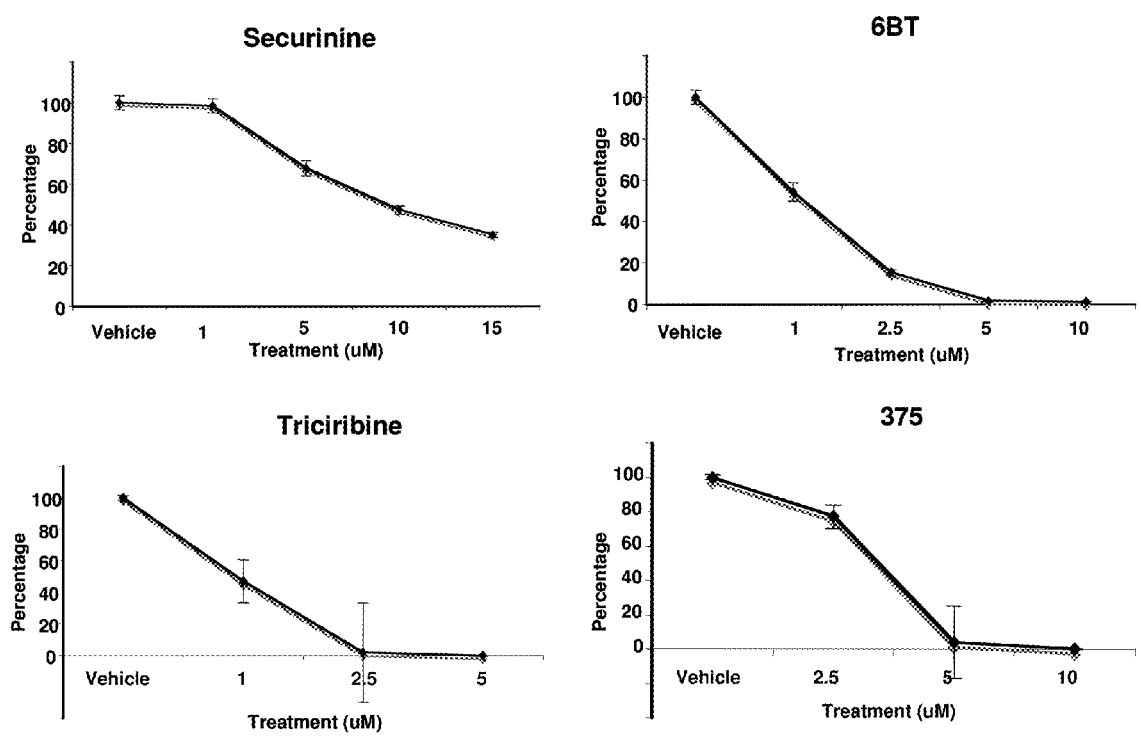
FIG. 6 illustrates plots showing differentiation-inducing compounds potently inhibit colony formation in soft agar. HL-60 cells were preincubated with the indicated compounds for 72 hours and the compound was removed and an equal number of viable cells was added to the soft agar. Plates were read for colony formation after 8 days. Results are expressed as percentage of colonies in the treated group compared vehicle control group.
Figure 9:
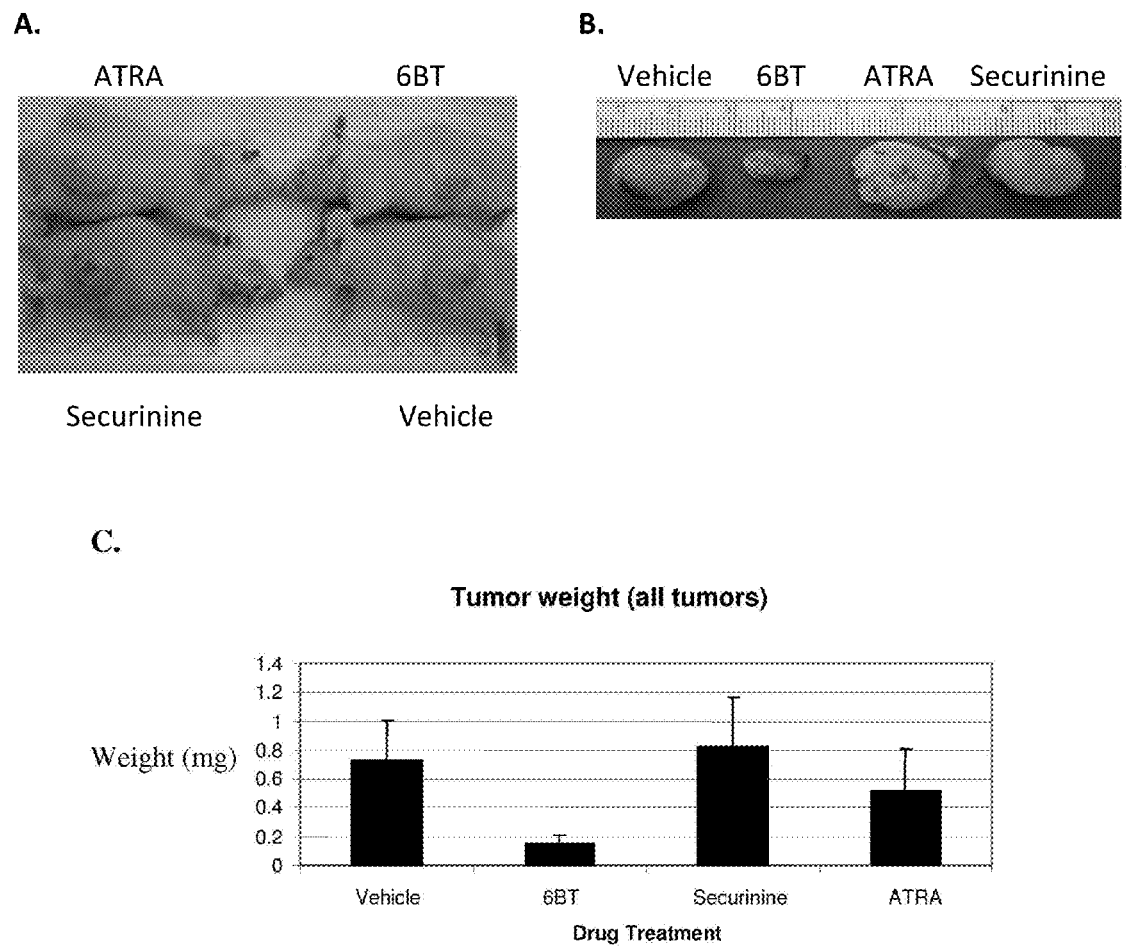
FIGS. 9(A-D) illustrate 6BT has potent in vivo effects. Nude mice (5 per experimental group) were injected with $5 \times 10^7$ HL-60 cells bilaterally into the flank. 9 days after tumor cell inoculation, the indicated drugs were injected I.P. three times a week for 3 weeks. (A). Representative picture of the mice at the end of the study period (B). Representative picture of tumors dissected from the indicated mice. (C). Average weights of tumors dissected from all mice (D). 6BT leads to evidence of in vivo differentiation.
Figure 10:
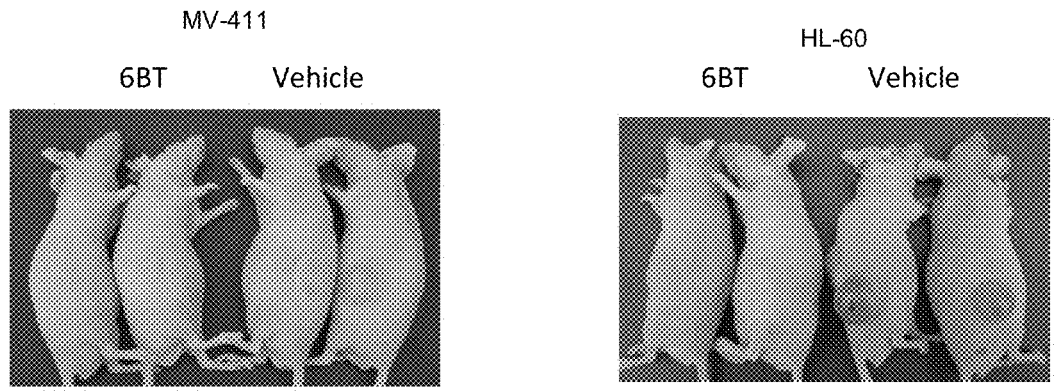
FIG. 10 illustrates images showing 6BT completely prevents MV4-11 and HL-60 tumor formation. Nude mice were (4 per experimental group) were injected with $5 \times 10^7$ HL-60 or MV411 cells bilaterally into the flank. One day after tumor cell inoculation, the indicated drugs were injected I.P. for 5 days followed by 3 times a week for 2 weeks. Representative pictures are shown after the mice were sacrificed at 4 weeks after tumor cell inoculation.

In order to assess how the compounds were inhibiting cell proliferation, cell cycle kinetics was assessed. As is common with the majority of known differentiation-inducers such as ATRA, 6BT, Securinine, and Triciribine lead to accumulation of cells in G0/G1. In contrast, 375 leads to accumulation in G2/M (FIG. 6).

In order to further assess the compounds abilities to induce terminal differentiation, soft agar colony assays were performed. (FIG. 6) All compounds were capable of significantly inhibiting colony formation and in several instances there was complete prevention of colony growth.

6BT and Securinine Synergize with Commonly Used Agents to Induce Differentiation The two compounds with the most clinical potential 6BT and securinine were studied further. If 6BT and/or securinine were used clinically for AML, it would likely be as a combination therapy with low dose chemotherapeutics or other differentiation-inducing agents. Therefore these compounds were tested for their ability to synergize with 1,25-dihydroxyvitamin D3, ATRA and several other currently used therapeutics that can induce low levels of myeloid differentiation (Table 3 and data not shown). Decitabine, a drug that is currently in clinical use for myelodysplastic syndrome, is a DNA methylation inhibitor. This agent may enhance the ability of differentiation agents to turn on genes necessary for myeloid differentiation as it can open up the chromatin. Low concentrations of either 6BT or Securinine are capable of enhancing the differentiation induced by both ATRA and decitabine as measured by the NBT reduction assay (Table 3). Both compounds also synergize in the upregulation of CD 11b as measured by flow cytometry (data not shown).

comparison significant differentiation or cell death effects upon the leukemic cells in our studies occurs at ~10 µM 6BT analogues have also been shown to have extremely low in vitro and mouse in vivo toxicity in studies examining their potential as Toxoplasma infection therapeutics.

In order to further assess the toxicity of 6BT and Securinine, normal human lymphocytes, normal human bone marrow, mouse embryonic fibroblasts, and human umbilical vein endothelial cells were examined. In all cases, 6BT had extremely low toxicity while securinine induced cell death occurred at doses higher than those required for activity on leukemia cells (figsdf).

Structure Activity Relationship (SAR) Studies

To begin to assess the structural requirements of 6BT for differentiation-inducing activity 20 analogs of 6BT that had various substitutents on the benzyl group were evaluated (generously provided by Dr. Mahmoud El Kouni, University of Alabama). All of the analogs had a complete loss of differentiation-inducing activity except for analogues 16 and 20 that had the addition of a chlorine or fluorine (FIG. 3 and FIG. 8). This work indicates the benzyl group plays an important role in the differentiation activity of 6BT.

TABLE 3

6BT and Securinine can synergize with ATRA and Decitabine to induce differentiation. HL-60 cells were treated with the indicated compounds for 4 days and the NBT reduction assay was performed. ATRA and decitabine both enhance differentiation induced by a low concentration of 6BT (3a) and Securinine (3b).

| ATRA | ATRA alone (%) | ATRA + 6BT µM (%) | Decitabine | Decitabine alone (%) | Decitabine + 6BT (1 µM(%) |
|---|---|---|---|---|---|
| 250 nM | 59 | 89 | 100 ng/ml | 26 | 77 |
| 80 nM | 37 | 83 | 50 ng/ml | 23 | 52 |
| 26 nM | 16 | 38 | 10 ng/ml | 14 | 43 |
| 9 nM | 9 | 31 | | | |
| 3 nM | 7 | 27 | | | |
| | Untreated 7% | | | Untreated 7% | |
| | 6BT alone 20% | | | 6BT alone 20% | |

6BT and Securinine Show Activity on Multiple AML Cell Lines and Primary Patient Samples 6BT and securinine were also found to be effective in differentiating other AML cell lines besides HL-60 cells, as well as primary patient leukemic samples (FIG. 7). In several cases, the compounds were able to induce a higher amount of differentiation than ATRA. It should be noted, that though ATRA is only clinically useful for APL, it is well known to potently induce the differentiation of many other AML cell lines in vitro. Interestingly, specific leukemic cell lines and primary patient samples quicly undergo cell death in response to 6BT and securinine. Though the exact mechanisms are not yet clear, certain leukemic cells appear to preferentially undergo cell death in response to 6BT and Securinine prior to full differentiation.

6BT and to a Lesser Extent Securinine have Extremely Low In Vitro Toxicity

As some leukemic cells appear to undergo rapid cell death in response to these compounds, it was important to assess their in vitro toxicity profile. To assess if the cell death is specific to leukemic cells, multiple cell lines were tested. In agreement with our data, both compounds previously have been analyzed for in vitro toxicity using the NCI-60 cell line screen. The NCI screen demonstrated extremely low toxicity of 6BT and Securinine with an average LD50 across the 60 cancer cell lines of 99 µM and 97 µM respectively with the highest concentration used in the screen being 100 µM. In Though Securinine has been used clinically in other countries for neurologic disorders, it is known to both lead to seizures and have an extremely rapid metabolism in vivo. For this reason we tested whether the stereoisomers virosecurinine and allosecurinine could also induce differentiation. Both of these compounds have decreased GABA A receptor affinity that is known to be associated with the seizure side effect and are thought to have different metabolic properties.

TABLE 4

Virosecurinine and allosecurinine both induce differentiation in HL-60 cells. HL-60 cells were treated with the indicated compounds for 10 days and the NBT reduction assay was performed.

| | NBT (%) | |
|---|---|---|
| Concentration (µM) | Virosecurinine | Allosecurinine |
| 10 | 95% | 80% |
| 5 | 99% | 50% |
| 2.5 | 50% | 40% |
| 1.25 | 30% | 25% |
| 0.06 | 20% | 20% |

6BT Exhibits Potent In Vivo Activity

In order to further assess the in vivo potential of 6BT and Securinine, mouse xenograft experiments were performed. In the first model, the ability of 6BT and Securinine to inhibit established HL-60 subcutaneous leukemic tumor growth in nude mice was assessed. In this model system, 6BT, but not Securinine was found to have significant in vivo activity. Interestingly, 6BT was significantly more effective than ATRA using this particular model even though high doses of ATRA were employed (30 mg/kg). In the second model system, the ability of 6BT to prevent either HL-60 or MV-411 tumor formation in nude mice was assessed. In this model system, 6BT was able to completely prevent tumor formation of both cell lines. Though studies to assess the optimal dosing regimen and formal toxicity studies have yet to be performed, the mice appeared to tolerate the 6BT. The mice lost a small amount of weight during the initial period of drug treatment, however, this weight was rapidly regained within a week of discontinuation of the drug.

Mechanism of Action

Figure 11:
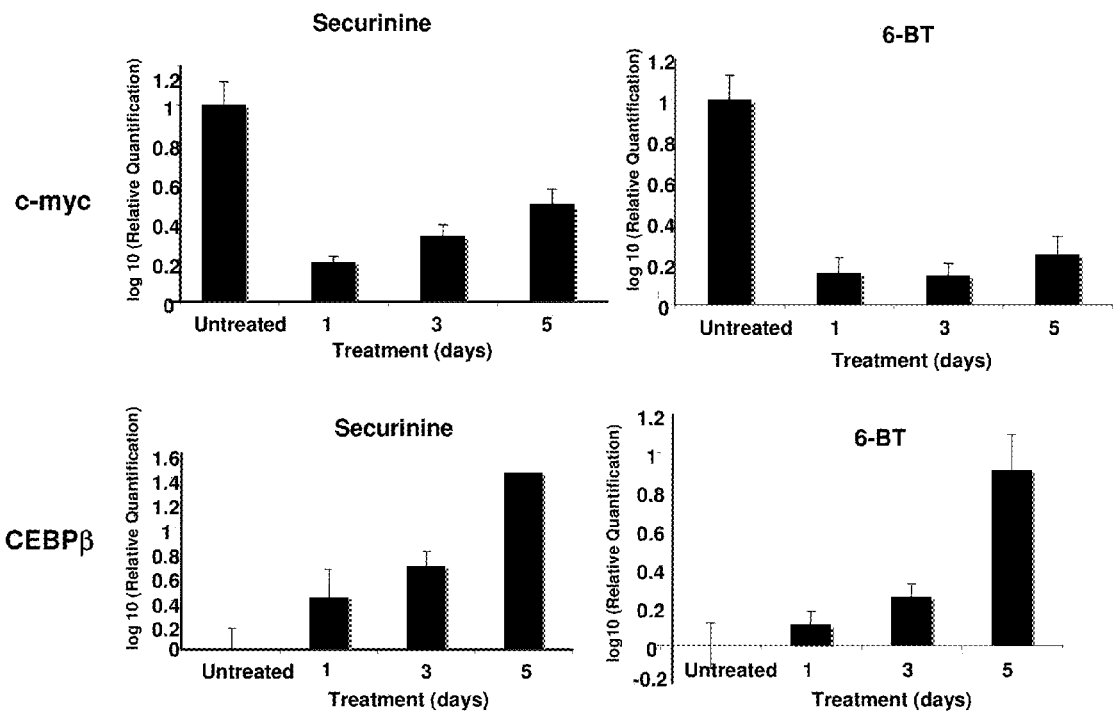
FIG. 11 illustrates graphs showing securinine and 6BT downregulate c-myc expression and upregulate CEBPB. HL-60 cells were treated with the indicated compounds for 1, 3, or 5 days and total RNA was prepared. The relative expression of c-myc and CEPβ was determined by real time PCR.

6BT and Securinine have Shared Downstream Signaling Pathways with Know Differentiation-inducers As 6BT and securinine compounds are structurally unrelated to previously described differentiation-inducing agents, the mechanisms of action are not completely clear. However, preliminary data demonstrates several known signaling pathways initiated by other differentiation-inducing agents such as ATRA and vitamin D3 are also activated by 6BT and Securinine. As both 6BT and Securinine induce evidence of monocytic differentiation, the expression of the transcription factor, CEBPβ that is known to be critical for monocytic differentiation was investigated. Both 6BT and Securinine were found to induce a time-dependent upregulation of CEBPβ. Similarly, the transcription factor c-myc which is important in regulating cell proliferation is known to be downregulated during terminal differentiation. Both 6BT and securinine were found to potently downregulate c-myc (FIG. 11).

Figure 12:
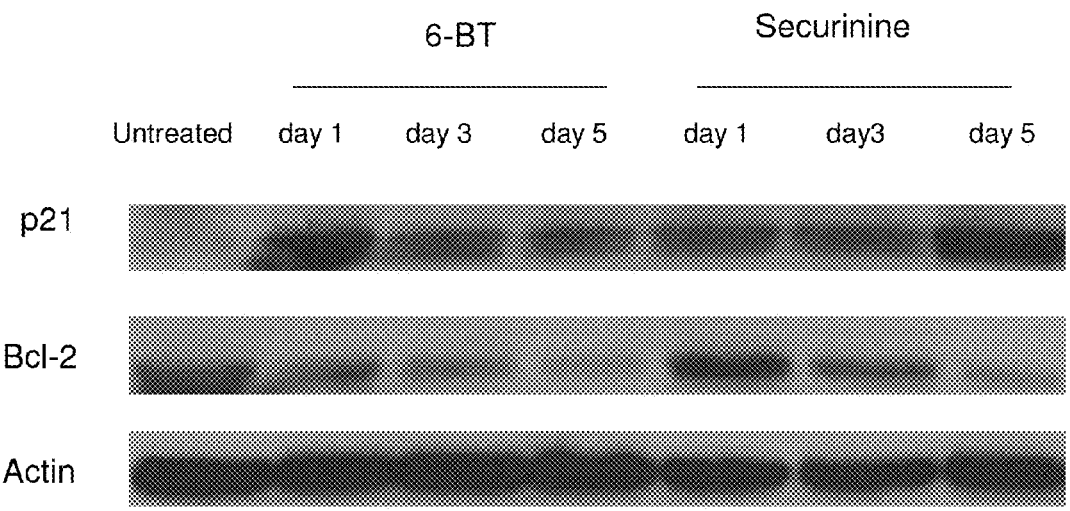
FIG. 12 illustrates an immunoblot showing 6BT and Securinine induce the upregulation of p21 and downregulation of Bcl-2. HL-60 cells were treated with the indicated compounds for 1, 3, or 5 days and cells were lysed. Western blot analysis was performed with p21, Bcl-2, and actin antibodies.

Both 6BT and Securinine were found to cause cells to accumulate in the G0/G1 phase of the cell cycle. As the protein p21 is known to block G1 to S phase transition by repressing the cyclin D/CDK4/6 complex, the expression level of p21 was examined. As is common with other differentiation-inducing compounds such as ATRA, the p21 protein was upregulated by both 6BT and securinine (FIG. 12).

Figure 13:
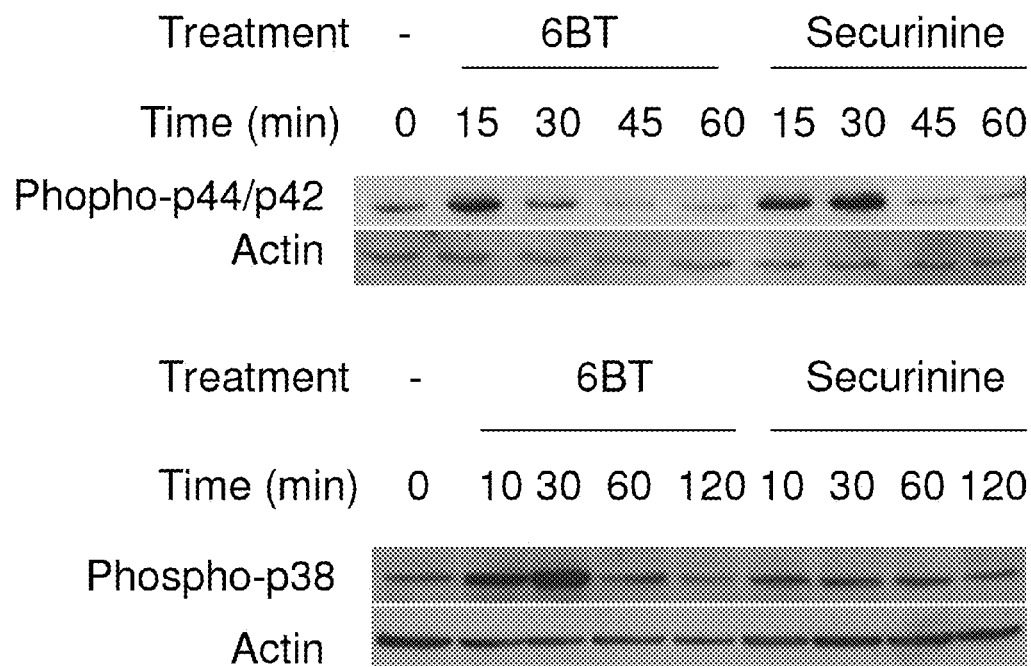
FIG. 13 illustrates an immunoblot showing 6BT and Securinine activate both p44/p42 and p38. HL-60 cells were treated with the indicated compounds for 15, 20, 46, or 60 minutes and the cells were lysed. Western blot analysis was performed with phospho-specific antibodies to p44/p42 and p38 as well as the actin anibody.
Figure 14:
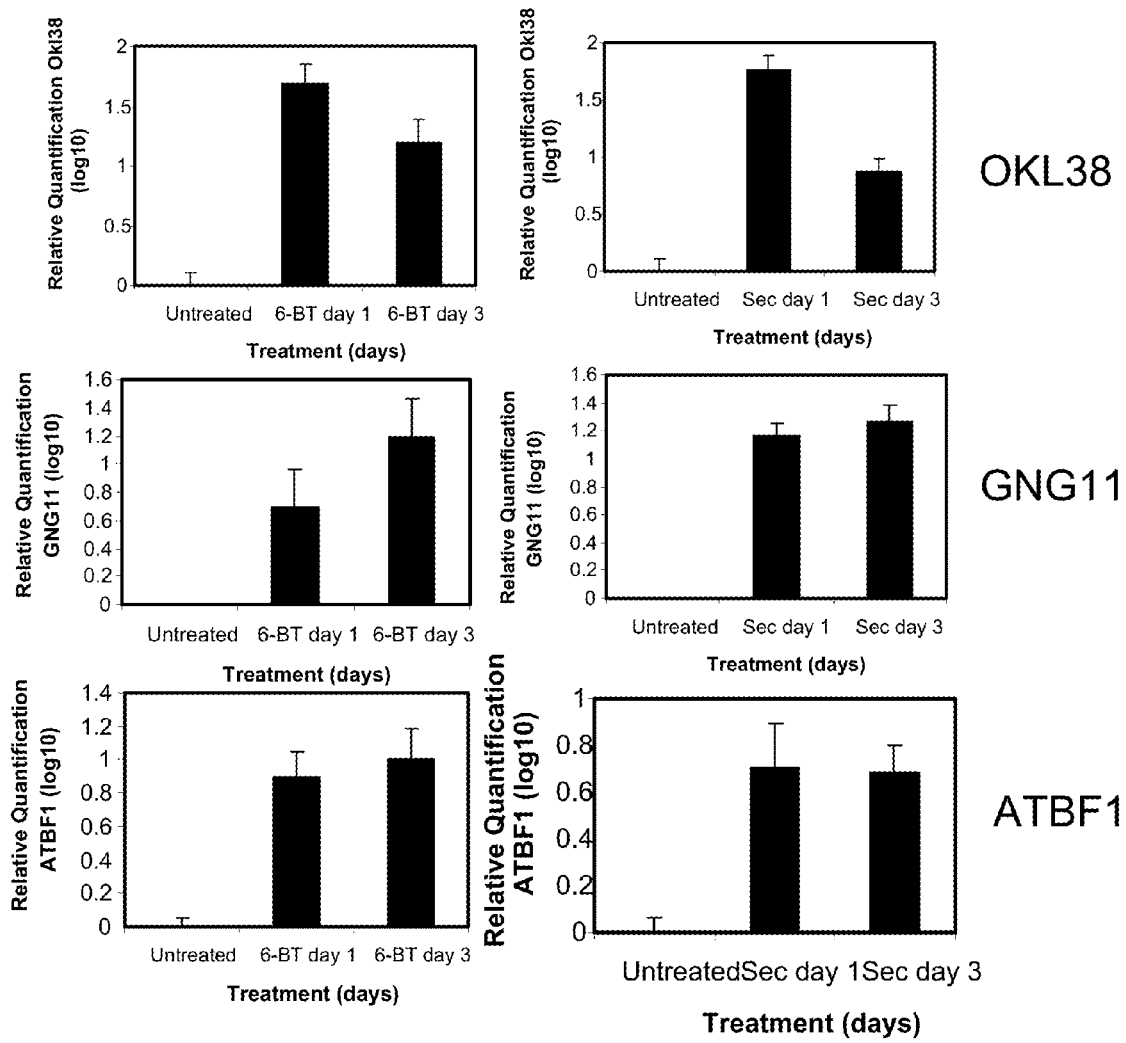
FIG. 14 illustrates graphs showing 6BT and securinine regulate the expression of genes that may play important roles in myeloid differentiation. HL-60 cells were treated with the indicated compounds for 1 or 3 days and total RNA was prepared. The relative expression of the indicated genes was assessed by real time PCR.

Finally, several other characterized differentiation-inducers, activate MAPK signaling pathways. As seen in FIG. 13, both 6BT and Securinine induce rapid phosphorylation of p44/p42 and p38.

6BT and Securinine Mediated Gene Expression Elucidates Novel Genes Potentially Involved in Myeloid Differentiation In order to further assess the signaling pathways of 6BT and securinine as well as to further elucidate the myeloid differentiation program in general, gene microarray studies were performed. These initial studies assessed the gene expression pattern at 16 and 72 hours after treatment. From this analysis both compounds induced the expected gene expression pattern resulting from monocytic differentiation (tablex). Both compounds induced a remarkably similar gene expression pattern at these timepoints. This finding indicates that though the initial signaling pathways initiated by these compounds is likely different, the end effect, monocytic differentiation, produces a very similar gene expression pattern. Furthermore, the expression of a large number (X) of previously unreported genes were found to be strongly regulated by 6BT and securinine. Several of these genes are known to be involved in the differentiation of non-hematopoietic cells such as neuron, muscle, and or keratinocyte differentiation. Selected examples of genes whose expression is strongly regulated by securinine and 6BT that have been verified is seen in FIG. 2.

For example, ATBF1 has been found to be important for neuronal and myogenic differentiation. As ATBF1 is also known to physically interact with the transcription factor, myb, that plays a key role in hematopoietic differentiation, it is possible that ATBF1 functions in myeloid differentiation.

Other examples of genes that may play important roles in myeloid terminal differentiation are OKL38 and GNG11 that have been found to be important for the proliferation of breast cancer cells and fibroblasts respectively. Finally, the kinase p38delta was found to be upregulated by both 6BT and securinine. Interestingly, it has been reported that the p38delta isoform, but not p38alpha or p38beta, plays a key role in keratinocyte differentiation. In addition, it was demonstrated that p38 is activated by 6BT and securinine. Further work will explore if the delta isoform is activated by these compounds.

Example 2

This Example assed the effects of securinine and its analogues in mice. We could not detect any significant effects of once a day administration of securinine (20 mg/kg) on the growth of HL-60 subcutaneous tumors in nude mice. HL-60 cell is an AML cell line commonly used for in-vitro studies and typically they are classified as M2 subtype. The dose utilized 20 mg/kg, had no evident toxicities, however a dose approximately two fold higher was found to lead to seizures due to securinine's affinity for the GABAA receptor. Therefore this was the highest dose that could be safely utilized.

Figure 15:
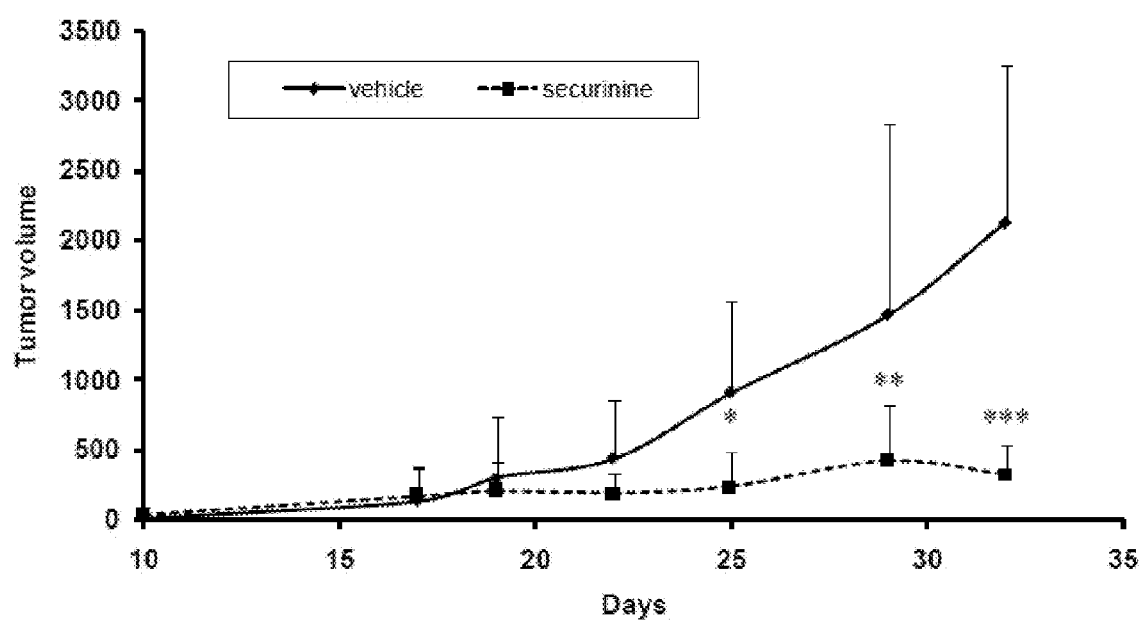
FIG. 15 illustrates a plot showing securinine significantly inhibits the growth of established AML tumors in nude mice.

Next we repeated the mouse xenograft experiments using i.p. drug administration (20 mg/kg), but with twice a day dosing again using HL-60 cell tumors. Securinine treated mice (n=5 mice, bilateral tumors), exhibited an average of more than 75% smaller tumors than vehicle treated mice at the end of the study period (FIG. 15). In contrast, experiments with twice a day dosing of ATRA (15 mg/kg) did not show any difference in tumor growth as compared to the vehicle treated mice.

Securinine (20 mg/kg) or vehicle (cytarabine-100 mg/kg) was injected i.p. into mice starting 10 days after HL-60 cell inoculation bilaterally into the flanks of nude mice (5 mice per group). Results shown represent the average size of tumors from the mice measured during the study period, * p=0.0075;  p=0.046; * p<0.001.

Around the time we confirmed securinine's in vivo activity using appropriate dosing, we discovered superior analogues of securinine that do not have the same propensity to cause seizures and exhibit higher potency. Thus additional mouse xenograft testing was proposed using the more optimized securinine compounds. Overall, though we encountered significant difficulty in assessing the effects of securinine in mice, we were successful in demonstrating that securinine exhibits promising in vivo activity at doses that do not cause any apparent toxic effects. It is highly likely that this activity will be significantly improved with our new securinine analogues that do not exhibit dose limiting seizure side effects and that in vivo differentiation can be more appropriately observed using a circulating model.

Effects of Securinine and its Analogues In Vitro

We were successful in synthesizing numerous securinine analogues during its structure activity relationship (SAR) studies that led to the identification of key portions of securinine that impact its activity. In particular we have identified two promising analogues that will form the basis of future lead optimization studies. The analogues that were successfully synthesized and their potency in inducing differentiation as measured by the NBT reduction assay using HL-60 cells are depicted in FIG. 16. The assays are done using the colorimetric process. The NBT reduction assay measures the respiratory burst and is done by stimulating the respiratory burst in cells with PMA and then looking for a color change in the NBT dye.

The vast majority of securinine analogues tested had significantly reduced activity as compared to the parent compound. It was found that the intact ring structures of securinine are important for its activity as a number of the compounds consisting of different intermediates used in the total synthesis of securinine had extremely low activity. In addition, attempts were made to eliminate the double bonds present in securinine as it was thought that this may reduce securinine's cytotoxicity. However, simple elimination of these double bonds also led to a significant reduction in activity. The only changes identified were additions to the 7 member ring. We found that several compounds with this modification had either nearly similar or in one case higher differentiation activity than the parent compound.

It was found that compound 2B which was approximately 6 times more potent than securinine in inducing differentiation remarkably still exhibits a very similar in vitro toxicity pattern to securinine. In addition, we found that compound 2A which exhibits equivalent differentiation-inducing activity to securinine has significantly reduced in vitro toxicity. In fact, compound 2A led to essentially no appreciable cell death in all cells that were tested up to the highest dose tested to date, (50 microM).

Compound 2A and compound 2B like securinine have favorable in vitro toxicity profiles. The different cell types were treated with increasing doses of securinine, compound 2A, and compound 2B for 72 hours and cell death was measured by tryphan blue exclusion to estimate the LD50.

TABLE 5

| | LD 50 | | |
|---|---|---|---|
| | Securinine | Compound 2A | Compound 2B |
| HCT116 | 30 | >>50 | 30 |
| HUVEC | 40 | >>50 | 40 |
| YAMC | 50 | >>50 | 45 |
| Lymphocytes | 50 | >>50 | >50 |
| MCF7 | 30 | >>50 | 30 |
| 293 | 30 | >>50 | 35 |

Figure 17:
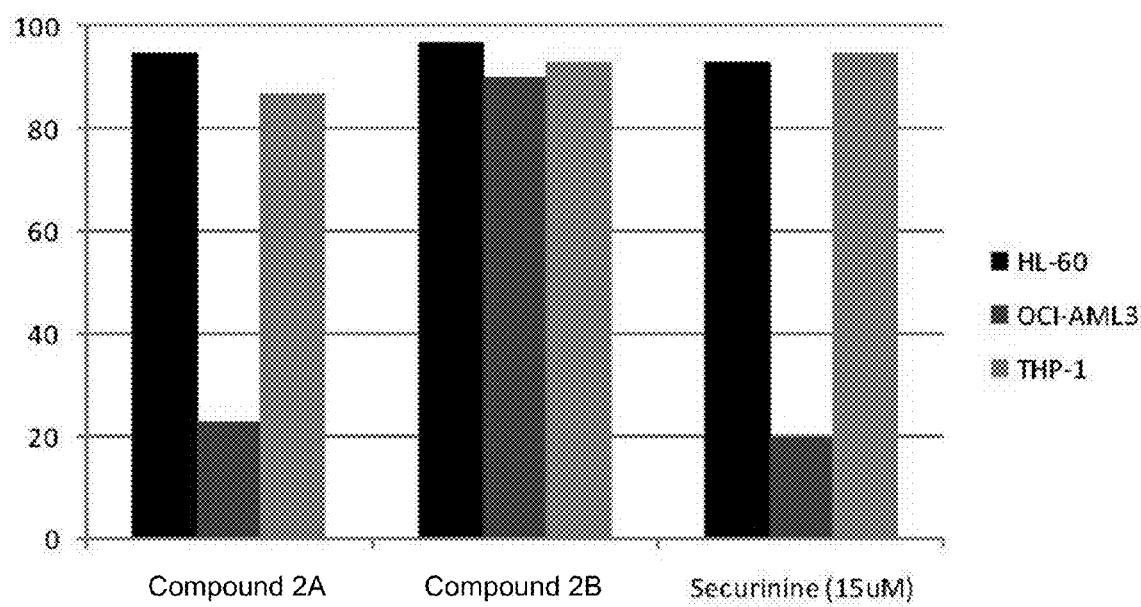
FIG. 17 illustrates a graph showing the comparison of differentiation of compound 2A and compound 2B and securinine.

The two most promising compounds (compound 2A and compound 2B) were further tested for their differentiation activity in several additional AML cell lines as compared to securinine (FIG. 17). Of particular note, compound 2B not only showed higher potency than securinine and the other analogues tested in all three cell lines tested, but it also showed higher differentiation activity in OCI-AML3 cells for which securinine only exhibits modest differentiation activity. In all three cell lines tested, a dose of only 2.5 uM of compound 2B was sufficient to induce nearly complete differentiation.

The above indicated cells were treated for 4 days and the NBT reduction assay was performed. The X-axis refers to the cell treatments and the Y-axis denotes the percentage of differentiation as measured by the NBT Reduction assay.

We performed a preliminary test with the two most promising analogues, compound 2A and compound 2B to verify their safety. We found that injection of 60 mg/kg (the highest dose tested due to limited amounts of these analogues), did not cause any evidence of toxic effects including seizures. As a comparison, a dose of 40 mg/kg of securinine will induce seizures.

We then tested the effects of securinine on patient samples. We were able to achieve its objective of demonstrating that securinine has activity in primary patient samples, this work was however hindered by the quality of patient specimens obtained. Unfortunately, many of the patient samples were not suitable for analysis. A significant portion of the cells that were obtained were either nonviable or contaminated with bacteria. Despite these obstacles, it was found that securinine induced differentiation in 8 of 10 leukemia patient samples that were suitable for analysis.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A method of inducing myeloid differentiation in a subject comprising: administering to a subject having acute myeloid leukemia a therapeutically effective amount of at least one of securinine or a securinine analogue having the following formula:

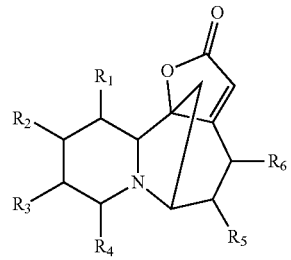

$R_1$, $R_2$, $R_3$, $R_4$, $R_5$, and $R_6$ are the same or different and are each selected from the group consisting of hydrogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O$^-$), C$_1$-C$_{24}$ alkylsulfanyl (—S-alkyl), arylsulfanyl (—S-aryl), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$_2$), phosphonato (—P(O)(O$^-$)$_2$), phosphinato (—P(O)(O$^-$)), phospho (—PO$_2$), phosphino (—PH$_2$), and combinations thereof;

wherein adjacent R groups may be linked to form a cyclic or polycyclic ring, wherein the ring is a substituted or unsubstituted aryl, a substituted or unsubstituted heteroaryl, a substituted or unsubstituted cycloalkyl, and a substituted or unsubstituted heterocyclyl; and pharmaceutically acceptable salts thereof.

2. The method of claim 1, wherein the securinine or securinine analogue has the following formula:

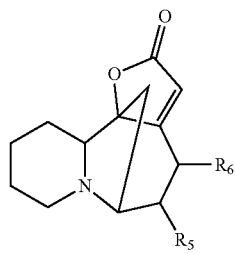

R$_5$ and R$_6$ are the same or different and are each selected from the group consisting of hydrogen, substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl (including C$_2$-C$_{24}$ alkylcarbonyl (—CO-alkyl) and C$_6$-C$_{20}$ arylcarbonyl (—CO-aryl)), acyloxy (—O-acyl), C$_2$-C$_{24}$ alkoxycarbonyl (-(CO)—O-alkyl), C$_6$-C$_{20}$ aryloxycarbonyl (—(CO)—O-aryl), C$_2$-C$_{24}$ alkylcarbonato (—O—(CO)—O-alkyl), C$_6$-C$_{20}$ arylcarbonato (—O—(CO)—O-aryl), carboxy (—COOH), carboxylato (—COO$^-$), carbamoyl (—(CO)—NH$_2$), C$_1$-C$_{24}$ alkyl-carbamoyl (—(CO)—NH(C$_1$-C$_{24}$ alkyl)), arylcarbamoyl (—(CO)—NH-aryl), thiocarbamoyl (—(CS)—NH$_2$), carbamido (—NH—(CO)—NH$_2$), cyano(—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), C$_1$-C$_{24}$ alkyl amino, C$_5$-C$_{20}$ aryl amino, C$_2$-C$_{24}$ alkylamido (—NH—(CO)-alkyl), C$_6$-C$_{20}$ arylamido (—NH—(CO)-aryl), imino (—CR=NH where R is hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, aralkyl), arylimino (—CR=N(aryl), where R=hydrogen, alkyl, aryl, alkaryl, etc.), nitro (—NO$_2$), nitroso (—NO), sulfo (—SO$_2$-OH), sulfonato (—SO$_2$-O$^-$), C$_1$-C$_{24}$ alkylsulfanyl (—S-alkyl), arylsulfanyl (—S-aryl), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P(O)(OH)$^2$) phosphonato (—P(O)(O$^-$)$_2$), phosphinato (—P(O)(O$^-$)), phospho (—PO$_2$), phosphino (—PH$_2$), and combinations thereof; and pharmaceutically acceptable salts thereof.

3. The method of claim 1, wherein the securinine or securinine analogue is selected from the group consisting of:

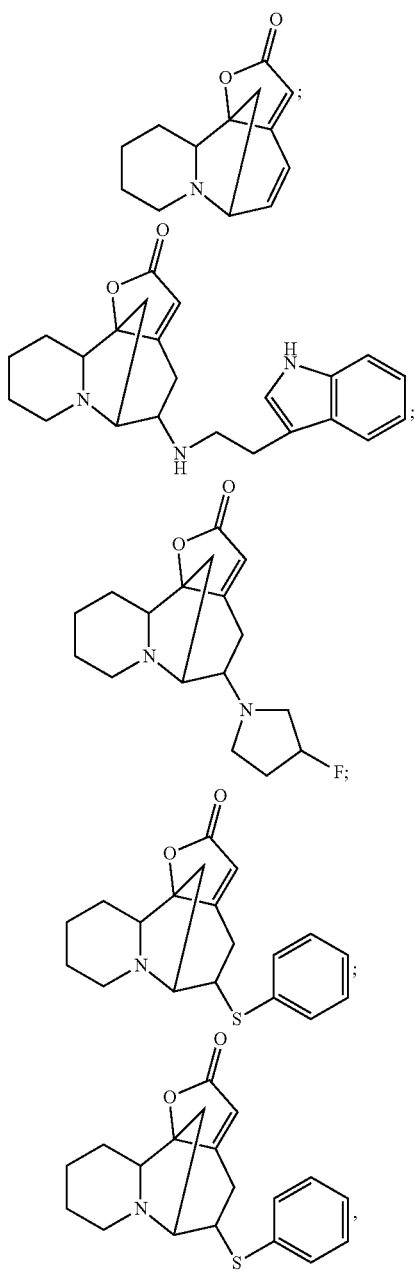

and pharmaceutically acceptable salts thereof.

4. The method of claim 1, wherein the securinine or securinine analogue includes a compound having the following formula:
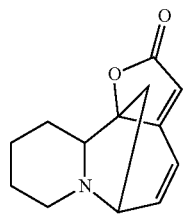 [SMILES: O=C1C=C2C=CC3CC2(O1)C1CCCCN31]
and pharmaceutically acceptable salts thereof.
* * * * *